(12) United States Patent
Glufke et al.

(10) Patent No.: US 6,949,677 B2
(45) Date of Patent: Sep. 27, 2005

(54) ACETOACETYLATED N-PHENYL-P-PHENYLENEDIAMINES

(75) Inventors: Uta Glufke, Basel (CH); Paul Hanselmann, Brig-Glis (CH)

(73) Assignee: Lonza AG, Basel (CH)

( * ) Notice: Subject to any disclaimer, the term of this patent is extended or adjusted under 35 U.S.C. 154(b) by 0 days.

(21) Appl. No.: 10/761,399

(22) Filed: Jan. 22, 2004

(65) Prior Publication Data

US 2004/0152919 A1 Aug. 5, 2004

Related U.S. Application Data

(62) Division of application No. 10/182,916, filed as application No. PCT/EP01/01163 on Feb. 2, 2001, now Pat. No. 6,734,324.
(60) Provisional application No. 60/203,922, filed on May 12, 2000.

(30) Foreign Application Priority Data

Feb. 4, 2000 (EP) ............................ 00102418

(51) Int. Cl.$^7$ ............................ C07C 233/05
(52) U.S. Cl. .................... 564/200; 564/199
(58) Field of Search ................. 564/199, 200

(56) References Cited

U.S. PATENT DOCUMENTS

| | | | |
|---|---|---|---|
| 2,115,413 A | 4/1938 | Dahlen et al. | |
| 3,702,365 A | 11/1972 | Thiele | |
| 5,466,268 A | 11/1995 | Cherpeck | |
| 5,637,121 A | 6/1997 | Cherpeck | |
| 2003/0030033 A1 * | 2/2003 | Duyck et al. | 252/380 |

FOREIGN PATENT DOCUMENTS

WO    WO 01/49761 A1 *  7/2001

OTHER PUBLICATIONS

C.E. Kaslow et al., J. of Am. Chem. Soc., (1946), 68, 644–547.
C.E. Kaslow et al., J. of Am. Chem. Soc., (1945), 67, 1969–1972.
N. Etkin et al., J. Org. Chem., (1990), 55, 1093–1096.
Thiele, Kurt, Database Chemabs 'Online'. Chemical Abstract: Service. Columbus, Ohio. U.S., SStn. Database Accession No. 70;68180.

* cited by examiner

*Primary Examiner*—Shailendra Kumar
(74) *Attorney, Agent, or Firm*—Fisher Christen & Sabol

(57) ABSTRACT

Compounds of the general Formula:

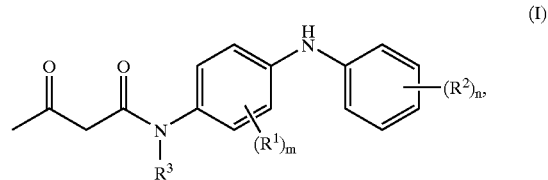

(I)

in which
$R^1$ and $R^2$ are at each occurrence independently hydroxyl, $C_{1-6}$-alkyl, $C_{1-6}$-alkoxy, halogen, phenyl or phenoxy;
$R^2$ is hydroxyl, $C_{1-6}$-alkyl, $C_{1-6}$-alkoxy, halogen, phenyl or phenoxy;
$R^3$ is $C_{1-6}$-alkyl;
m is an integer from 0 to 4; and
n is an integer from 0 to 5.

5 Claims, No Drawings

ACETOACETYLATED N-PHENYL-P-PHENYLENEDIAMINES

This is a division of U.S. Ser. No. 10/182,916, filed on Oct. 21, 2002, now U.S. Pat. No. 6,734,324, that is a 371 of PCT/EP01/01163, filed on Feb. 2, 2001, that has benefit of U.S. Provisional No. 60/203,922, filed on May 12, 2000, and that has priority benefit of European Patent Application No. 60102418.1, filed on Feb. 4, 2000.

The present invention relates to a process for the preparation of acetoacetylated aromatic amines, in particular of acetoacetylated N-phenyl-p-phenylenediamines, and novel acetoacetylated N-phenyl-p-phenylenediamines.

U.S. Pat. No. 2,115,413 describes the reaction of ethyl acetoacetate with N-phenyl-p-phenylenediamine for the preparation of 3-oxo-N-[4-(phenylamino)phenyl]-butyramide.

C. E. Kaslow et al. describes the reaction of primary aromatic amines with diketene for the preparation of acetoacetanilides in *J. Am. Chem. Soc.* 1946, 68, 644–647.

C. E. Kaslow et al. describes the reaction of secondary aromatic amines with diketene for the preparation of N-alkylacetoacetanilides in *J. Am. Chem. Soc.* 1945, 67, 1969–1970. The reaction is also described by N. Etkin et al. in *J. Org. Chem.* 1990, 55, 1093–1096. The secondary aromatic amines employed here are alkyl- or alkoxy-substituted anilines. The reaction of N—$C_{1-6}$-alkyl-3-oxo-N-[4-(phenylamino)phenyl]butyramides is not described.

The object of the present invention was to make available a process for the preparation of acetoacetylated N-phenyl-p-phenylenediamines. The object is achieved by the of the invention.

The process relates to the preparation of compounds of the general formula

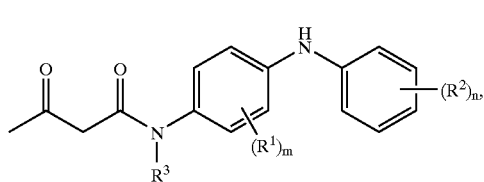

(I)

in which
$R^1$ and $R^2$ are at each occurrence independently hydroxyl, $C_{1-6}$-alkyl, $C_{1-6}$-alkoxy, halogen, phenyl or phenoxy;
$R^3$ is hydrogen or $C_{1-6}$-alkyl.
m is an integer from 0 to 4; and
n is an integer from 0 to 5.

These compounds can exist in at least two tautomeric forms (keto-enol tautomerism), whereas for simplification only the keto form, respectively, is mapped here. However, the invention comprises all tautomers and their mixtures.

The process is characterized in that diketene is reacted with an N-phenyl-p-phenylenediamine of the general formula

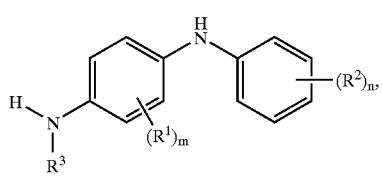

(II)

in which $R^1$, $R^2$, $R^3$, m and n have the meaning indicated above, in the presence of 3–40% strength acetic acid at temperatures of 20 to 100° C., preferably at 60 to 70° C.

$C_{1-6}$-Alkyl is understood here and below as meaning all linear or branched alkyl groups having 1–6 carbon atoms such as, for example, methyl, ethyl, propyl, isopropyl, butyl, isobutyl, sec-butyl, tert-butyl, pentyl, isopentyl, tert-pentyl, neopentyl, hexyl or isohexyl.

$C_{1-6}$-Alkoxy is understood as meaning groups which are composed of $C_{1-6}$-alkyl and oxygen, such as, for example, methoxy, ethoxy, propoxy, isopropoxy, butoxy, sec-butoxy or tert-butoxy.

The variables m and n have preferably the value 0 (zero). The radical $R^3$ is preferably $C_{1-6}$-alkyl, particularly preferably isopropyl.

The addition of the diketene surprisingly only takes place at the nitrogen atom which carries the radical $R^3$.

The compound of the formula II in which m=n=0 and $R^3$ is hydrogen are commercially obtainable, e.g. from Fluka, the remaining compounds can be prepared according to known methods, e.g. by reaction of aniline or substituted aniline with nitrobenzene or azobenzene and subsequent hydrogenation. The compounds of the formula II in which $R^3$ is $C_{1-6}$-alkyl can be prepared according to known methods, e.g. by reductive alkylation of N-phenyl-p-phenylenediamines of the formula II ($R^3$=H) with an aliphatic ketone or aldehyde.

The compounds of the formula I in which $R^3$ is $C_{1-6}$-alkyl are novel and likewise a subject of the invention. These compounds can be employed, for example as additives for fuels of internal combustion engines. A further possibility of use is afforded as drying accelerators for polymers.

The compounds of the formula I can be converted by reaction with ammonia into the corresponding enamines of the general formula

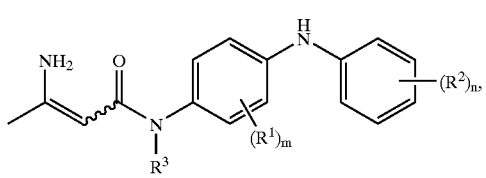

(III)

in which $R^1$, $R^2$, $R^3$, m and n have the meaning indicated above. These enamines can exist as two geometric isomers (E and Z-configuration at the enamine double bond), whereas here the two isomers as well as their mixtures are comprehended. Preferably, the Z-configuration is formed.

The reaction with ammonia is expediently carried out at temperatures from 10 to 150° C., preferably at approximately 70° C., and pressures from 1 to 100 bar, preferably at 10 to 30 bar. The reaction is expediently carried out in a suitable solvent in the presence of catalytic amounts of conc. or aqueous acetic acid. Suitable solvents are, for example, esters, aromatic and aliphatic hydrocarbons, chlorinated aliphatic hydrocarbons, ethers and polyethers, alcohols and also water. Preferably, ethyl acetate is employed as a solvent. Expediently, 0.02–2.0 mol of conc. acetic acid are employed based on 1 mol of the compound of the formula I.

The compounds of the formula III in which $R^3$ is $C_{1-6}$-alkyl are novel and likewise a subject of the invention.

By means of catalytic hydrogenation of the compounds of the formula III, compounds of the general formula

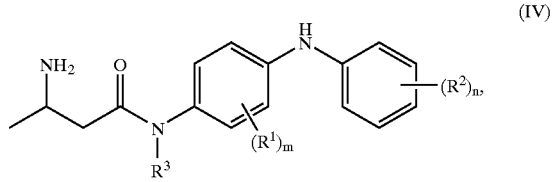

(IV)

in which $R^1$, $R^2$, $R^3$, m and n have the meaning indicated above, are formed.

The catalytic hydrogenation is carried out at temperatures from 100 to 200° C., preferably at approximately 110° C., and pressures of 20 to 150 bar, preferably of approximately 100 bar. A suitable hydrogenation catalyst is Raney nickel. The hydrogenation is expediently carried out in a suitable solvent in the presence of a base, preferably in the presence of ammonia. Suitable solvents are for example aliphatic alcohols or mixtures of water and aliphatic alcohols, methanol being preferably employed.

The compounds of the formula IV in which $R^3$ is $C_{1-6}$-alkyl are novel and likewise a subject of the invention.

The following examples illustrate the implementation of the process according to the invention and the preparation of the compounds according to the invention, without being regarded as restricting them.

EXAMPLE 1

3-Oxo-N-[4-phenylamino)phenyl]butyramide (I, m=n=0, $R^3$=H)

A) Simultaneous Addition of the Starting Materials

Diketene (160.13 g, 1.904 mol) and a solution of N-phenyl-p-phenylenediamine (344.00 g, 1.867 mol) in 40% strength acetic acid (1300.00 g) were simultaneously added dropwise at 60° C. in the course of about 4.5 h to 40% strength acetic acid (300.00 g). After addition of the starting materials had taken place, the reaction mixture was stirred at 65° C. for 30 min and then cooled to 15° C. The resulting precipitate was filtered off on a suction filter, washed with 40% strength acetic acid (2×200 g) and with water (2×200 g) and dried at 50° C. in vacuo (20 mbar). 415.31 g (95.3% content, 79% yield) of 3-oxo-N-[4-(phenylamino)phenyl] butyramide were obtained as a light grey solid. Mp: 89.5° C.;

$^1$H-NMR (400 MHz, DMSO-$d_6$)δ=13.89 (s, 0.1 H, $OH_{enol}$), 9.93 (s, 0.9 H, $NH_{keto}$), 9.87 (s, 0.1 H, $NH_{enol}$), 8.02 (s, 1.0 H, NH), 7.50–7.42 (m, 2 H, Ar—H), 7.25–7.16 (m, 2 H, Ar—H), 7.10–6.98 (m, 4 H, Ar—H), 6.80–6.70 (m, 1 H, Ar—H), 5.18 (s, 0.1 H, CO—CH=COH), 3.53 (s, 1.9 H, CO—$CH_2$—CO), 2.12 (s, 2.7 H, $CH_{3keto}$), 1.90 (s, 0.3 H, $CH_{3enol}$).

B) Non-Simultaneous Addition of the Starting Materials

Diketene (18.6 g, 0.221 mol) was added dropwise at 60° C. to a solution of N-phenyl-p-phenylenediamine (40.00 g, 0.217 mol) in 40% strength acetic acid (100.00 g) in the course of 40 min. The reaction mixture was stirred at 65° C. for 30 min and cooled to 15° C. The very viscous suspension was filtered. The precipitate was washed with 40% strength acetic acid (2×25 g) and water (2×25 g) and dried at 50° C. in vacuo (20 mbar). 53.50 g (92% yield) of 3-oxo-N-[4-(phenylamino)phenyl]butyramide were obtained as a light grey solid. Mp: 93.0° C.

EXAMPLE 2

N-Isopropyl-3-oxo-N-[4-(phenylamino)phenyl] butyramide (I, m=n=0, $R^3$=isopropyl)

Diketene (261.10 g, 3.105 mol) was added dropwise at 60° C. to a solution of N-(isopropylamino)-N-phenyl-p-phenylenediamine (388.00 g, 1.714 mol) in 40% strength acetic acid (1200 ml) in the course of 2 h. After addition of the diketene had taken place, the reaction mixture was stirred at 65° C. for 2.5 h and cooled to 5° C. overnight. The resulting precipitate was filtered off on a suction filter, washed with water (2×150 ml) and dried at 40° C. in vacuo (20 mbar). 400.60 g (75% yield) of N-isopropyl-3-oxo-N-[4-(phenylamino)phenyl]butyramide were obtained as a dark grey solid.

$^1$H-NMR (400 MHz, CDCl$_3$)δ 14.48 (s, 0.1 H, $OH_{enol}$), 7.35–7.25 (m, 2 H, Ar—H), 7.20–7.10 (m, 2 H, Ar—H), 7.10–6.95 (m, 3 H, Ar—H), 6.95–6.90 (m, 2 H, Ar—H), 6.01 (s, 1 H, NH), 5.05–4.92 (m, 1 H, CH(CH$_3$)$_2$), 4.45 (s, 0.1 H, CO—CH=COH), 3.21 (s, 1.9 H, CO—CH$_2$—CO), 2.10 (s, 2.7 H, $CH_{3keto}$), 1.89 (s, 0.3 H, $CH_{3enol}$), 1.09 (d, J=8.2 Hz, 6H, CH(CH$_3$)$_2$).

EXAMPLE 3

(Z)-3-Aminobut-2-enoic acid N-isopropyl-N-[4-(phenylamino)phenyl]amide (III, m=n=0, $R^3$= isopropyl)

N-Isopropyl-3-oxo-N-[4-(phenylamino)phenyl]-butyramide (30.0 g, 0.0967 mol) and conc. acetic acid (1.4 g, 0.0233 mol) in ethyl acetate (140 g) were introduced into an autoclave. Ammonia (16.0 g, 0.9395 mol) was introduced in the course of 10 minutes and the temp. of the reaction mixture was increased to 35° C. during this period. After the introduction a pressure of 14 bar is present. The temperature of the reaction mixture was heated to 70° C. in the course of 30 min. In the course of this, the pressure rose to 17 bar. After 2.5 h under these conditions, the reaction mixture was cooled to 25° C. and ammonia was released. The reaction mixture was further cooled to 5° C. in order to crystallize the product. The suspension was filtered. The pale grey solid was washed with cold (0° C.) ethyl acetate (20 ml) and dried in vacuo (50 mbar) at 35° C. for 2 days. (Z)-3-Aminobut-2-enoic acid N-isopropyl-N-[4-(phenylamino)phenyl]amide (27.2 g, 91.0%) was obtained.

$^1$H-NMR (400 MHz, CDCl$_3$) δ 7.36–7.25 (m, 2 H, Ar—H), 7.18–7.11 (m, 2 H, Ar—H), 7.09–7.02 (m, 2 H, Ar—H), 6.99–6.96 (m, 3 H, Ar—H), 5.84 (s, 1 H, NH), 5.05–4.99 (m, 1 H, CH(CH$_3$)$_2$), 4.04 (s, 1 H, CO—CH=C), 1.71 (s, 3 H, CH$_3$), 1.03 (d, J=8 Hz, 6 H, CH(CH$_3$)$_2$).

EXAMPLE 4

3-Amino-N-isopropyl-N-[4-(phenylamino)phenyl] butyramide (IV, m=n=0, $R^3$=isopropyl)

(Z)-3-Aminobut-2-enoic acid N-isopropyl-N-[4-(phenylamino)phenyl]amide (13.9 g, 0.0449 mol) and Raney nickel (K0840 Ni B113W) (2.0 g) in methanol (140 g) were introduced into an autoclave. Ammonia (5.5 g, 0.3230 mol) was introduced in the course of 5 minutes. The temperature of the reaction mixture was 25° C. The pressure rose to 5 bar. After the introduction of ammonia, the reaction mixture was warmed to 80° C. (no further pressure rise). Hydrogen was injected at 80° C. until the pressure was 100 bar. The reaction mixture was heated to 110° C. and stirred at this temperature for 4.5 h. In the course of this, a pressure of 100 bar was maintained by continuous injection of hydrogen. The reaction mixture was cooled to 25° C. and the pressure was carefully let down. The reaction mixture was filtered off and the filtrate was concentrated to one half. The concentrate was treated with 1 g of active carbon, stirred for 1 h, filtered and concentrated to dryness. 12.8 g of crude product were obtained, which was melted at 175° C. The melt could be crystallized on an aluminium foil. 11.1 g of 3-amino-N-isopropyl-N-[4-(phenylamino)phenyl]butyramide (79.3%) were obtained.

$^1$H-NMR (400 MHz, CDCl$_3$) δ 7.38–6.90 (m, 9 H, Ar—H), 6.03 (s, 1 H, NH), 5.05–4.95 (m, 1 H, CH(CH$_3$)$_2$), 3.42–3.32 (m, 1 H, CH—NH$_2$), 2.10–1.90 (m, 2 H, COCH$_2$), 1.53 (bs, 2 H, NH$_2$), 1.03 (d, J=8 Hz, 6 H, CH(CH$_3$)$_2$), 0.98 (d, J=8 Hz, 3 H, CH$_3$).

What is claimed is:

1. A compound of the formula:

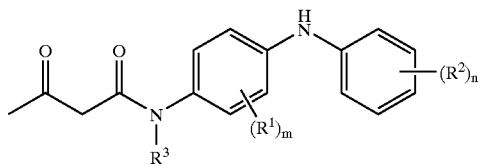

(I)

in which

R$^1$ and R$^2$ are at each occurrence independently hydroxy, C$_{1-6}$-alkyl, C$_{1-6}$-alkoxy, halogen, phenyl or phenoxy;

R$^3$ is C$_{1-6}$-alkyl;

m is an integer from 0 to 4; and n is an integer from 0 to 5.

2. The compound according to claim 1, wherein R$^3$ is isopropyl.

3. The compound according to claim 1, wherein R$^3$ is methyl.

4. The compound according to claim 1, wherein R$^3$ is selected from the group consisting of ethyl, propyl, butyl, isobutyl, sec-butyl, tert-butyl, pentyl, isopentyl, tert-pentyl, neopentyl, hexyl and isohexyl.

5. The compound according to claim 1, wherein R$^3$ is isopropyl, m is 0 and n is 0.

* * * * *